Patented July 22, 1941

Plant Pat. 479

UNITED STATES PATENT OFFICE

479

PEACH TREE

Frederick Wenzl Hof Mann, Blacksburg, Va.

No Drawing. Application September 17, 1940, Serial No. 357,294

1 Claim. (Cl. 47—62)

The present invention relates to a new and distinct variety of peach tree, the result of a definite effort over a number of years to obtain by crossing and selection a peach fruit without pubescence but having other desirable characteristics which are important from a commercial standpoint.

More specifically, this new peach is of the varietal type of the Elberta, Hale or related group originating from a cross of Greensboro seedling and Elberta, recrossing a fuzzless progeny on Hale and then selection from progeny of this cross. The primary feature of the new variety resides in the plum-like, waxy, and smooth or non-fuzz surface of the fruit skin.

This new variety is clearly distinguishable from other peach varieties of this type, including the variety Candoka, by the fact that the skin of the fruit is microscopically, as well as macroscopically, free of any bristle, fuzz or pubescence, thus giving the fruit a smooth, plum-like, fuzzless, waxy skin coat long before and at maturity.

Another point of distinction of importance is found in the foliar glands of the peach tree. Although there may be some variation in the character, number and shape of these glands, the usual number of these glands comprises three opposite pairs, with the first pair reniform, the second between reniform to globose, and the third globose, and in those cases of variation in the number from these three pairs with more glands, those glands very low on the petiole are glands of reniform type, and those farther up on the foliage toward the leaf tip are smaller globose.

In addition to this, the new peach variety is an improvement over the Elberta in winter hardiness, in the greater hardiness of the fruit buds to winter kill, in the greater hardiness of the blossoms to spring freezes, as well as frosts, in the high resistance to brown rotting of the fruit, and a type of flesh characteristic that allows for less danger from break down in the steps from harvesting to final marketing.

Because of its very high degree of resistance to brown rot and other break-down decay fungi, it is possible to delay picking for a greater period, allowing for a higher degree of maturity, quality, and richness, as well as delectability of flavor. Again, this resistance, together with the firm type of flesh, adapts this new variety as a prime fruit for dessert either in a fresh or preserved state. Because of the decline in dried peach consumption, due to the presence of fuzz, this invention offers promise of greater and more orderly consumption of the dehydrated product.

Asexual reproduction of this variety shows that the characteristics herein set forth are established.

In view of the similarity to the Elberta and Hale varieties, and the intangible nature of the majority of the novel characteristics, illustration of the peach is unnecessary, particularly in view of the following detail description thereof, wherein color terminology conforms with general dictionary standards.

It may be stated that the development work leading to this origination was carried out in the States of Nebraska and Virginia, and the observations herein made relate to those specimens grown by me at Blacksburg, Virginia.

Tree: Large to medium. Vigorous. Upright to spreading. Open to dense. Vase formed. Hardy. Very productive to productive. Regular bearer.

*Trunk.*—Stocky. Medium to shaggy, more shaggy with age.

*Branches.*—Stocky. Smooth, but more shaggy with age. Brown-Gray for older branches, Green-Gray Brown for younger. Dull. *Lenticels*—medium in number. Large to medium in size.

*Leaves.*—Length—6½ to 7 inches. Width—2 to 2½ inches. Large. Ovate. Lanceolate to spatulate. Abruptly and acutely pointed. Thick. Medium to Dark Green. Rugose. *Margin*—glandular. Finely serrate. *Petiole*—long to medium. Thick. *Glands*—average number—four to six arranged in pairs. Opposite but vary some. First two large; second two medium; last two small. First two reniform, rest globose. Red and Green, to Brown when older. *Position*—from lower leaf to and on petiole. *Stipules*—none.

Flower-buds.—Hardy. Large to medium. Medium to short. Obtuse. Plump. Appressed. Pubescent.

Flowers.—Dates first and full bloom—April 21–April 25. Late compared with other varieties. Medium to small. Pink to Salmon (size and color much like Elberta).

Fruit: August 26 to September 1, but can be left as much as ten days for full tree ripening without impairing keeping or shipping properties.

*Size.*—Uniform to slightly variable. Large, some medium (average with size of Elberta and Hale). Diameter axial—2¾ to 3 inches. Transverse in suture plane—2½ to 3 inches. At right angles to suture plane—2¾ to 3¼ inches.

*Form.*—Uniform to slightly variable. Symmetrical to slightly unsymmetrical. Globose to oblate. (Like Elberta-Hale.)

*Suture.*—Distinct line. (Like Elberta-Hale.)

*Ventral surface.* — Rounded slightly to strongly lipped toward base, apex throughout both sides. *Lips*—equal to unequal. (Like Elberta-Hale.)

*Cavity.*—Rounded to abrupt, somewhat circular. Elongated in suture plane with suture showing on both sides. Depth—⅛ to $\frac{3}{16}$ inch. Breadth—⅛ to $\frac{3}{16}$ inch.

*Base.*—Rounded to truncate.

*Apex.*—Short; rounded to truncate. *Pistil point*—apical. (Like Elberta-Hale.)

*Stem.*—Length—¼ inch. Stout. Glabrous. *Adherence to stone*—strong. (Like Elberta-Hale.)

*Skin.*—Thick. Tenacious to flesh. *Tendency to crack*—none in wet or dry seasons. *Color*—Yellow Gold. Absolutely devoid of any skin fuzz, down, or pubescence whatever. A smooth glabrous fuzzless or non-fuzz Elberta-Hale peach type. Skin is sweet and edible.

*Flesh.*—*Color*—Yellow Honey Gold. No red at pit margin, clear yellow throughout. *Surface of pit cavity*—Yellow, throughout. *Amygdalin* — abundant to moderate. *Juice*—moderate, rich. *Texture*—firm; fine; meaty. *Fibres*—fine. *Ripens*—even to some uneven; earliest at apex along both lips. *Flavor*—slightly subacid; mild; delicate; vinous. *Aroma*—pronounced. *Eating quality*—good to best.

Stone: Free.

*Fibres.*—Short. Parts from flesh smoothly.

*Size.*—Medium.

*Length.*—1½ to ¾ inches.

*Breadth.*—1¼ inches.

*Thickness.*—¼ inch.

*Form.*—Globose, oval to elliptical; cuneate toward base.

*Base.*—Straight. *Hilum*—broad to moderate. *Apex*—acute to acuminate.

*Sides.*—Equal to slightly unequal; regularly furrowed throughout; ridged throughout; pitted throughout.

*Ridges.*—Jagged.

*Seeds.*—Elongated.

*Ventral edge.*—Thick with wing toward base throughout.

*Dorsal edge.*—Full with moderately deep groove. Ridges on either side—mostly continuous.

*Color of stone.*—Brown.

*Tendency to split.*—Only slight in wet season.

Use: Market, local, dessert, culinary, canning.

Keeping quality: Good.

Resistance to:

*Insects.*—Same as with Elberta and Hale.

*Diseases.*—Good—very high resistance to brown rot and storage break-down.

Shipping quality: Good.

I claim:

A new and distinct variety of peach tree characterized as to novelty by the non-fuzz, plum-like, waxy and smooth skin of its fruit, the firmness of the flesh of such fruit, the winter hardiness of the tree, hardiness of bud and blossom to spring freezes and frosts, the form and number of glands, and resistance to brown rot, substantially as described.

FREDERICK WENZL HOF MANN.